(12) United States Patent
Kessler et al.

(10) Patent No.: US 10,010,192 B1
(45) Date of Patent: Jul. 3, 2018

(54) UNIVERSAL FIT DISPOSABLE SEAT PADS, METHODS OF MAKING AND METHODS OF USING SAME

(71) Applicants: Matthew Kessler, Easton, PA (US); Michelle Kessler, Easton, PA (US)

(72) Inventors: Matthew Kessler, Easton, PA (US); Michelle Kessler, Easton, PA (US)

(*) Notice: Subject to any disclaimer, the term of this patent is extended or adjusted under 35 U.S.C. 154(b) by 0 days.

(21) Appl. No.: 15/836,561

(22) Filed: Dec. 8, 2017

(51) Int. Cl.
A61L 15/16 (2006.01)
A47C 31/00 (2006.01)
A47C 31/11 (2006.01)

(52) U.S. Cl.
CPC ........... *A47C 31/113* (2013.01); *A61L 15/16* (2013.01)

(58) Field of Classification Search
CPC ........ A47C 31/10–31/116; A61L 15/16; A61F 13/15–13/15772; A61F 2013/15008–2013/15195; C09J 2201/128
See application file for complete search history.

(56) References Cited

U.S. PATENT DOCUMENTS

| 3,853,595 | A | * | 12/1974 | Pedginski | ............ | C09J 7/0275 |
| | | | | | | 33/2 R |
| 4,079,739 | A | * | 3/1978 | Whitehead | ........ | A61F 13/15674 |
| | | | | | | 604/365 |
| 4,883,701 | A | | 11/1989 | Rankin et al. | | |
| 4,885,200 | A | | 12/1989 | Perdelwitz, Jr. et al. | | |
| 7,655,106 | B2 | * | 2/2010 | Nishiyama | ............... | C09J 7/02 |
| | | | | | | 156/231 |
| 7,677,661 | B1 | | 3/2010 | Ferrari-Cicero | | |
| 2003/0215600 | A1 | | 11/2003 | Ammons | | |

FOREIGN PATENT DOCUMENTS

WO  WO 2016166759  10/2016

* cited by examiner

*Primary Examiner* — Patricia L. Nordmeyer
(74) *Attorney, Agent, or Firm* — James R. McDaniel (57) ABSTRACT

A seat protection pad to protect a seat against spilled liquids and other bodily fluids including human and animal fluids, including a base pad having a first side and a second side and a front portion, a mid-section portion and a rear portion, wherein the base pad includes a base pad opening located between the mid-section portion and the front portion, an upper pad having a first side and a second side and a front end and a rear end, wherein the upper pad is attached to the first side of the base pad at a location adjacent to the front portion of the base pad such that the second side of the upper pad is located adjacent to the first side of the base pad, an upper pad opening located between the front end of the upper pad and the front portion of the base pad such that the upper pad opening is aligned with the base pad opening to allow a seat belt buckle to be inserted through the base pad opening and the upper pad opening, a plurality of adhesive strips located on the second side of the base pad, wherein a first one of the plurality of adhesive strips is attached adjacent to the rear portion of the base pad, a second one of the plurality of adhesive strips is attached adjacent to the mid-section portion of the base pad and a third one of the plurality of adhesive strips is attached adjacent to the front portion of the base pad, and a plurality of stitches located on each of the plurality of adhesive strips for securing the plurality of adhesive strips to the base pad.

19 Claims, 6 Drawing Sheets

UNIVERSAL FIT DISPOSABLE SEAT PADS, METHODS OF MAKING AND METHODS OF USING SAME

FIELD OF THE INVENTION

The present invention is generally related to a disposable seat pad. The disposable seat pad can be used on a variety of different types and sizes of seats. The disposable seat pad provides seat protection against liquids and other bodily fluids including humans and/or animals. The disposable pad includes strategically located adhesive strips that releasably secure the pad in place instead of using hooks, loops and the like in order to provide a universal fit for the pad on the seat. The disposable pad includes a super absorbent polymer that allows the disposable pad to absorb copious amounts of liquids. The disposable pad is shaped in such a manner so that the pad forms a "cup" when the pad is placed in a conventional children's car seat while also conforming to any other seat that an adult or child may use. The disposable pad is designed so that it does not interfere with the car seat straps while still preventing liquids from flowing into the car seat strap orifices. The disposable pad fits most current children's car seats, boosters etc. giving users confidence that it will fit the seat they own. The geometry and materials of the disposable pad allow for many seat pads to be stored together in a small place, such as the storage pocket on the back of the driver's seat. Finally, the disposable pad is constructed from materials that are acceptable to most municipal waste sites.

BACKGROUND OF THE INVENTION

Prior to the present invention, as set forth in general terms above and more specifically below, it is known, to employ various types of absorbent pads for seats. See for example, U.S. Pat. No. 4,885,200 by Perdelwitz, Jr. et al., U.S. Patent Application Publication 2003/0215600 by Ammons, and PCT Patent Application WO 2016/166759 by Dargatzky. While these various absorbent pads may have been generally satisfactory, there is nevertheless a need for a new and improved, universal fit disposable seat pad that can be used on a variety of different types and sizes of seats in order to provide seat protection against liquids and other bodily fluids including humans and/or animals.

It is a purpose of this invention to fulfill these and other needs in the disposable seat pad art in a manner more apparent to the skilled artisan once given the following disclosure.

BRIEF SUMMARY OF THE INVENTION

A first aspect of the present invention is a seat protection pad to protect a seat against spilled liquids and other bodily fluids including human and animal fluids, including a base pad having a first side and a second side and a front portion, a mid-section portion and a rear portion, wherein the base pad includes a base pad opening located between the mid-section portion and the front portion, an upper pad having a first side and a second side and a front end and a rear end, wherein the upper pad is attached to the first side of the base pad at a location adjacent to the front portion of the base pad such that the second side of the upper pad is located adjacent to the first side of the base pad, an upper pad opening located between the front end of the upper pad and the front portion of the base pad such that the upper pad opening is aligned with the base pad opening to allow a seat belt buckle to be inserted through the base pad opening and the upper pad opening, a plurality of adhesive strips located on the second side of the base pad, wherein a first one of the plurality of adhesive strips is attached adjacent to the rear portion of the base pad, a second one of the plurality of adhesive strips is attached adjacent to the mid-section portion of the base pad and a third one of the plurality of adhesive strips is attached adjacent to the front portion of the base pad, and a plurality of stitches located on each of the plurality of adhesive strips for securing the plurality of adhesive strips to the base pad.

In one embodiment of the first aspect of the present invention, the base pad and the upper pad further include a non-woven layer, a first tissue cellulose layer located adjacent to the non-woven layer, a super absorbent polymer layer located adjacent to the first tissue cellulose layer, a second tissue cellulose layer located adjacent to the super absorbent polymer layer, and a liquid barrier layer located adjacent to the first second cellulose layer.

In another embodiment of the first aspect of the present invention, the non-woven layer further includes polypropylene.

In another embodiment of the first aspect of the present invention, the super absorbent polymer layer further includes a fiber fluff cellulose pulp.

In another embodiment of the first aspect of the present invention, the liquid barrier layer further includes polyethylene.

In still another embodiment of the first aspect of the present invention, the plurality of adhesive strips further includes a first adhesive layer, a carrier layer located adjacent to the first adhesive layer, a second adhesive layer located adjacent to the carrier layer, and a removable liner layer located adjacent to the second adhesive layer.

In an even further embodiment of the first aspect of the present invention, the first adhesive layer includes a synthetic acrylic adhesive (SAA).

In yet another embodiment of the first aspect of the present invention, the carrier layer includes polyethylene terephthalate (PET).

In still another embodiment of the first aspect of the present invention, the second adhesive layer includes SAA.

In a yet another embodiment of the first aspect of the present invention, the removable liner layer includes a mono-axial oriented polypropylene (MOPP).

A second aspect of the present invention is a multi-layered, disposable seat pad for fluid collection, including a base pad having a first side and a second side and a front portion, a mid-section portion and a rear portion, wherein the base pad includes a base pad opening located between the mid-section portion and the front portion, an upper pad having a first side and a second side and a front end and a rear end, wherein the upper pad is attached to the first side of the base pad at a location adjacent to the front portion of the base pad such that the second side of the upper pad is located adjacent to the first side of the base pad, an upper pad opening located between the front end of the upper pad and the front portion of the base pad such that the upper pad opening is aligned with the base pad opening to allow a seat belt buckle to be inserted through the base pad opening and the upper pad opening, a plurality of adhesive strips located on the second side of the base pad, wherein a first one of the plurality of adhesive strips is attached adjacent to the rear portion of the base pad, a second one of the plurality of adhesive strips is attached adjacent to the mid-section portion of the base pad and a third one of the plurality of adhesive strips is attached adjacent to the front portion of the base pad, and a plurality of stitches located on each of the plurality of adhesive strips for securing the plurality of adhesive strips to the base pad.

In one embodiment of the second aspect of the present invention, the base pad and the upper pad further include a non-woven layer, a first tissue cellulose layer located adjacent to the non-woven layer, a super absorbent polymer layer located adjacent to the first tissue cellulose layer, a second tissue cellulose layer located adjacent to the super absorbent polymer layer, and a liquid barrier layer located adjacent to the second cellulose layer.

In another embodiment of the second aspect of the present invention, the non-woven layer further includes polypropylene.

In another embodiment of the second aspect of the present invention, the super absorbent polymer layer further includes a fiber fluff cellulose pulp.

In another embodiment of the second aspect of the present invention, the liquid barrier layer further includes polyethylene.

In still another embodiment of the second aspect of the present invention, the plurality of adhesive strips further includes a first adhesive layer, a carrier layer located adjacent to the first adhesive layer, a second adhesive layer located adjacent to the carrier layer, and a removable liner layer located adjacent to the second adhesive layer.

In an even further embodiment of the second aspect of the present invention, the first adhesive layer includes a synthetic acrylic adhesive (SAA).

In yet another embodiment of the second aspect of the present invention, the carrier layer includes polyethylene terephthalate (PET).

In still another embodiment of the second aspect of the present invention, the second adhesive layer includes SAA.

A third aspect of the present invention is a method of using a releasable seat protection pad to protect a seat against spilled liquids and other bodily fluids including human and animal fluids, including the steps of: providing a base pad having a first side and a second side and a front portion, a mid-section portion and a rear portion, wherein the base pad includes a base pad opening located between the mid-section portion and the front portion; providing an upper pad having a first side and a second side and a front end and a rear end, wherein the upper pad is attached to the first side of the base pad at a location adjacent to the front portion of the base pad such that the second side of the upper pad is located adjacent to the first side of the base pad; providing an upper pad opening located between the front end of the upper pad and the front portion of the base pad such that the upper pad opening is aligned with the base pad opening to allow a seat belt buckle to be inserted through the base pad opening and the upper pad opening; providing a plurality of adhesive strips located on the second side of the base pad, wherein a first one of the plurality of adhesive strips is attached adjacent to the rear portion of the base pad, a second one of the plurality of adhesive strips is attached adjacent to the mid-section portion of the base pad and a third one of the plurality of adhesive strips is attached adjacent to the front portion of the base pad; providing a plurality of stitches located on each of the plurality of adhesive strips for securing the plurality of adhesive strips to the base pad; and releasably attaching the second side of the base pad to a seat, wherein the plurality of adhesive pads is releasably attached to the seat.

The preferred universal fit disposable seat pad, according to various embodiments of the present invention, offers the following advantages: ease of use; lightness in weight; durability; the ability to use the disposable seat pad on a variety of different types and sizes of seats; the ability of the disposable seat pad to provide seat protection against liquids and other bodily fluids including humans and/or animals; the use of strategically located adhesive strips that releasably secure the pad in place in order to provide a universal fit for the pad on the seat; the use of a super absorbent polymer that allows the disposable pad to absorb copious amounts of liquids; the disposable pad is shaped in such a manner so that the pad forms a "cup" when the pad is placed in a conventional children's car seat while also conforming to any other seat that an adult or child may use; the disposable pad is designed so that it does not interfere with the car seat straps while still preventing liquids from flowing into the car seat strap orifices; the disposable pad fits most current children's car seats, boosters etc. giving users confidence that it will fit the seat they own; the geometry and materials of the disposable pad allow for many seat pads to be stored together in a small place, such as the storage pocket on the back of the driver's seat; and the disposable pad is constructed from materials that are acceptable to most municipal waste sites. In fact, in many of the preferred embodiments, these advantages are optimized to an extent that is considerably higher than heretofore achieved in prior, known absorbent pads for seats.

BRIEF DESCRIPTION OF THE DRAWINGS

The above-mentioned features and steps of the invention and the manner of attaining them will become apparent, and the invention itself will be best understood by reference to the following description of the embodiments of the invention in conjunction with the accompanying drawings, wherein like characters represent like parts throughout the several views and in which.

DETAILED DESCRIPTION OF THE PREFERRED EMBODIMENTS OF THE INVENTION

In order to address the shortcomings of the prior, known absorbent pads for seats, reference is made now to FIGS.

1-6, where there is illustrated universal fit disposable seat pad 2. As will be explained hereinafter in greater detail, the universal fit disposable seat pad 2 can be used on a variety of different types and sizes of seats. The disposable seat pad 2 provides seat protection against liquids and other bodily fluids including humans and/or animals. The disposable pad 2 includes strategically located adhesive strips that releasably secure the pad 2 in place instead of using hooks, loops and the like in order to provide a universal fit for the pad on the seat. The disposable pad 2 includes a super absorbent polymer that allows the disposable pad 2 to absorb copious amounts of liquids. The disposable pad 2 is shaped in such a manner so that the pad forms a "cup" when the pad 2 is placed in a conventional children's car seat while also conforming to any other seat that an adult or child may use. The disposable pad 2 is designed so that it does not interfere with the car seat straps while still preventing liquids from flowing into the car seat strap orifices. The disposable pad 2 fits most current children's car seats, boosters etc. giving users confidence that it will fit the seat they own. The geometry and materials of the disposable pad 2 allow for many seat pads to be stored together in a small place, such as the storage pocket on the back of the driver's seat. Finally, the disposable pad 2 is constructed from materials that are acceptable to most municipal waste sites.

As shown in FIG. 1-6, there is illustrated universal fit disposable seat pad 2 that is constructed according to the present invention. Universal fit disposable seat pad 2 includes, in part, base pad 4, upper pad area 6, upper pad 8, upper pad area opening 10, base pad opening 12, peripheral pad stitching 14, upper pad stitching 16, upper pad stitching 18 and opening stitching 20.

Figure 1:
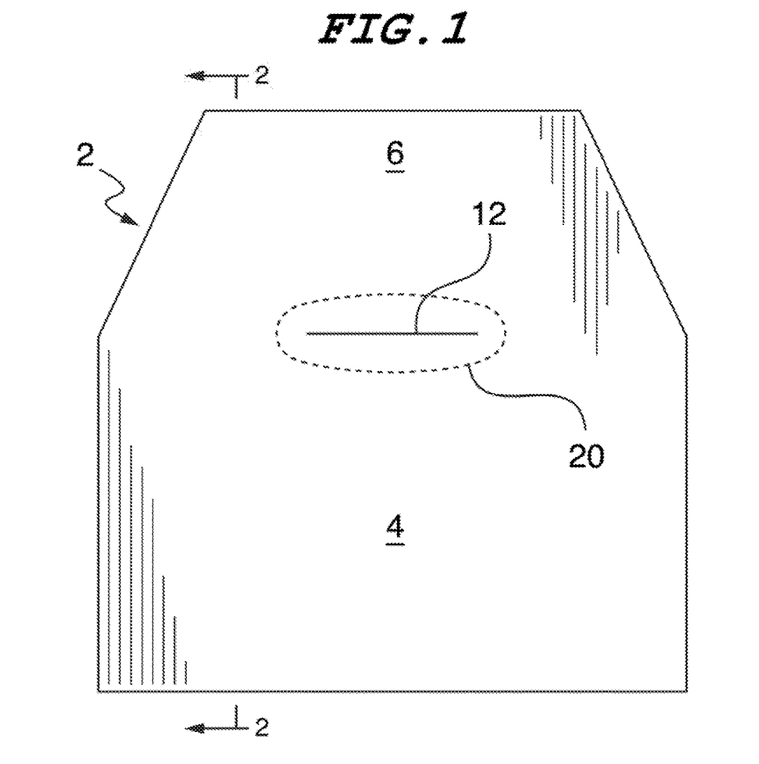
FIG. 1 is a top view of the base pad of a universal fit disposable seat pad, according to the present invention.
Figure 2:
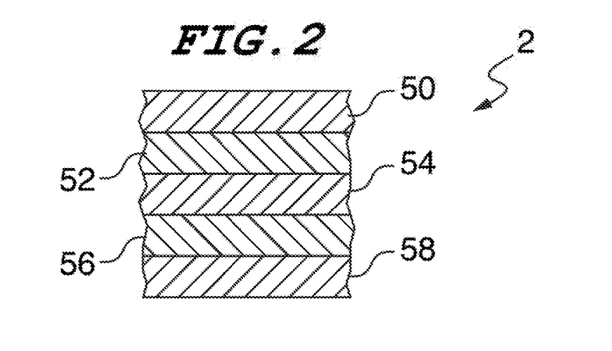
FIG. 2 is a side view of the universal fit disposable seat pad layers taken along lines 2-2 of FIG. 1, according to the present invention.

With respect to base pad 4 and upper pad area 6, as shown in FIGS. 1 and 2, base pad 4 includes base pad opening 12 and opening stitching 20. It is to be understood that base pad opening 12, preferably, is formed on base pad 4 by conventional cutting or forming techniques. A unique aspect of the present invention is that base pad opening 12 is formed in base pad 4 in order to allow a conventional seat belt buckle (not shown) to be placed through base pad opening 12, as will be discussed in greater detail later. It is to be further understood that a length and width of base pad 4 should be such that base pad 4 will properly fit over a conventional child's car seat or other types of seats while providing the proper protection against spilled liquids and other bodily fluids including humans and/or animals.

With respect to opening stitching 20, opening stitching 20 is conventionally formed around base pad opening 12. Preferably, opening stitching 20 is an interlock stitch but other well-known types of stitching can also be used. A yet even further unique aspect of the present invention is the use of opening stitching 20 around the base pad opening 12. In this manner, opening stitching 20 substantially prevents base pad opening 12 from ripping or tearing once the seat belt buckle is inserted through base pad opening 12 by providing a reinforcement for base pad opening 12.

Regarding the construction of base pad 4, as shown more clearly in FIG. 2, base pad 4 is constructed of several layers so that universal fit disposable seat pad 2 is able to absorb copious amounts of liquids. In particular, base pad 4, includes, in part, a non-woven layer 50, a tissue cellulose layer 52, a super absorbent polymer layer 54, a tissue cellulose layer 56, and a liquid barrier layer 58. It is to be understood that the various layers of base pad 4 are conventionally attached together to form the multi-ply construction of base pad 4.

With respect to non-woven layer 50, preferably, non-woven layer 50 is constructed of polypropylene. Preferably, the density of the polypropylene is at least 35 g/m$^2$. Another unique aspect of the present invention is that the non-woven layer 50 provides an outer layer of the base pad 4 that is durable and exhibits excellent tensile strength. It is to be understood that these properties of the non-woven layer 50 are important to universal fit disposable seat pad 2 because the legs and buttocks of the user (usually an infant or a child) will be directly contacting the non-woven layer 50 so this layer needs to be durable and have high tensile strength or else the outer, non-woven layer 50 will rip and/or tear, thereby rendering the universal fit disposable seat pad 2 unable to perform the desired absorption of the liquids.

With respect to tissue cellulose layers 52 and 56, preferably, tissue cellulose layers 52 and 56 are constructed of any suitable cellulose material. However, the important factor in the selection of the cellulose material being that the cellulose material must be able to wick away any liquids that come into contact with the cellulose layers 52 and 56. In particular, the tissue cellulose layers 52 and 56 must be able to wick away any liquid that comes into contact with the tissue cellulose layers 52 and 56 by causing the liquid to spread out across the surfaces of the tissue cellulose layers 52 and 56. In this manner, the liquid is not allowed to pool or otherwise collect in a small area on tissue cellulose layers 52 and 56.

Regarding super absorbent polymer layer 54, preferably, super absorbent polymer layer 54 is constructed as a composite with a fiber fluff cellulose pulp. Another unique aspect of the present invention is that the super absorbent polymer layer 54 is capable of absorbing copious amounts of liquid. A further unique aspect of the present invention is that the super absorbent polymer layer 54, in conjunction with the tissue cellulose layers 52 and 56, allows any liquids encountered by the universal fit disposable seat pad 2 to be uniformly and evenly spread out across the super absorbent polymer layer 54 and the tissue cellulose layers 52 and 56. In particular, as discussed above, any liquid that contacts tissue cellulose layers 52 and 56 is wicked and spread out across the surfaces of the tissue cellulose layers 52 and 56. As the liquid is spreading across the surfaces of the tissue cellulose layers 52 and 56, the liquid is then absorbed across the surface area of the super absorbent polymer layer 54. In this manner, the liquid is not allowed to pool or otherwise collect in a small area on tissue cellulose layers 52 and 56 and super absorbent polymer layer 54, thereby increasing the liquid absorbing capabilities of the universal fit disposable seat pad 2. It is to be understood that tissue cellulose layers 52 and 56 and super absorbent polymer layer 54 are to be constructed so that these layers, collectively, have an absorption of at least 120 ml/100 cm$^2$.

With respect to liquid barrier layer 58, preferably, liquid barrier layer 58 is constructed of polyethylene. Preferably, the density of the polyethylene is at least 45 g/m$^2$. A still further unique aspect of the present invention is that the liquid barrier layer 58 provides an outer layer of the base pad 4 that substantially prevents any liquids that have not been absorbed by tissue cellulose layers 52 and 56 and super absorbent polymer layer 54 from leaking out of universal fit disposable seat pad 2. Also, liquid barrier layer 58 should be constructed of a material that is durable and is capable of having adhesive strips attached thereto, as will be described in greater detail later. It is to be understood that these properties of the liquid barrier layer 58 are important to universal fit disposable seat pad 2 because the universal fit disposable seat pad 2 will be releasably attached to the seat across the surface of liquid barrier layer 58 so this layer needs to be durable or else the outer, liquid barrier layer 58 will rip and/or tear, thereby rendering the universal fit disposable seat pad 2 unable to perform the desired absorption of the liquids.

Figure 3:
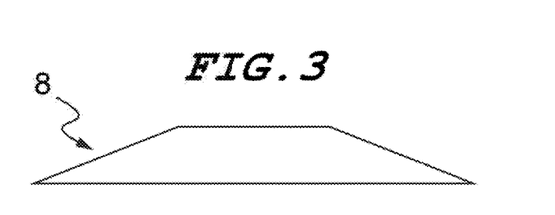
FIG. 3 is a top view of the upper pad of a universal fit disposable seat pad, according to the present invention.

With respect to FIG. 3, there is illustrated upper pad 8. It is to be understood that upper pad 8 is constructed in substantially the same manner as base pad 4. A still further unique aspect of the present invention is that upper pad 8 is formed so that it can be secured to upper pad area 6 by upper pad stitches 16 and 18, as will be described in greater detail later.

Figure 4:
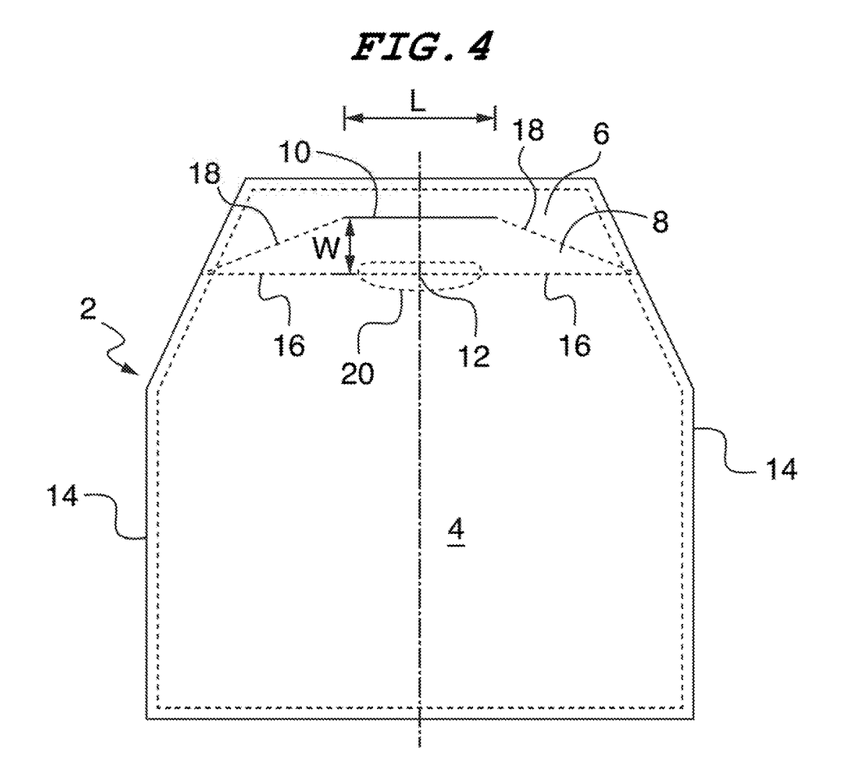
FIG. 4 is a top view of the universal fit disposable seat pad, constructed according to the present invention.

Regarding FIG. 4, there is illustrated universal fit disposable seat pad 2 with the upper pad 8 being attached to base pad 4. As shown in FIG. 4, upper pad 8 is attached to base pad 4 by upper pad stitches 16 and 18. Preferably, upper pad stitches 16 and 18 are, preferably, an interlock-type of stitching but other well-known types of stitching can also be used. It is to be further understood that stitching 14 is located around a periphery of universal fit disposable seat pad 2. In this manner, stitching 14 is used to further assist in keeping the various layers of base pad 4 attached together and provide an attractive edging for universal fit disposable seat pad 2.

Another unique aspect of the present invention is that universal fit disposable seat pad 2 includes upper pad area opening 10 and base pad opening 12. As will be discussed in greater detail later, upper pad area opening 10 and base pad opening 12 are aligned on universal fit disposable seat pad 2 so as to allow a seat belt buckle (not shown) to be easily inserted through base pad opening 12 and then through upper pad area opening 10 so as to allow the universal fit disposable seat pad 2 to be retained on the seat area of the seat and still allow the seat belt buckle to be operatively latched to the seat belt latch (not shown) so that the user of the seat can be securely retained in the seat.

A still further unique aspect of the present invention is that the use of upper pad area opening 10 and base pad opening 12 in conjunction with the seat belt buckle will create a blockage or dam around the area where the seat belt buckle interacts with the upper pad 8, the upper pad area opening 10 and base pad opening 12. In this manner, once the seat belt buckle has been inserted through upper pad area opening 10 and base pad opening 12, the locking of the seat belt buckle with the seat belt latch will cause the upper pad 8 to raise up and form a blockage or dam around the area located adjacent to the upper pad 8, the upper pad area opening 10, the base pad opening 12 and the seat belt buckle. This blockage or dam should assist in keeping any liquids that come into contact with the universal fit disposable seat pad 2 from leaving the universal fit disposable seat pad 2 at the raised-up area around the upper pad 8, the upper pad area opening 10, the base pad opening 12 and the seat belt buckle. It is to be understood that if the length (L) of the upper pad 8 is too long, a blockage or dam may not form at the raised-up area around the upper pad 8, the upper pad area opening 10, the base pad opening 12 and the seat belt buckle. Conversely, if the length (L) is too short, the universal fit disposable seat pad 2 may inadvertently become removed from the seat when the seat belt buckle is attached to the seat belt latch, which is not desirable. Furthermore, if the width (W) of the upper pad 8 is too short, a blockage or dam may not form at the raised-up area around the upper pad 8, the upper pad area opening 10, the base pad opening 12 and the seat belt buckle. Conversely, if the width (W) is too long, the universal fit disposable seat pad 2 may inadvertently become bunched at the at the raised-up area around the upper pad 8, the upper pad area opening 10, the base pad opening 12 and the seat belt buckle which may cause an uncomfortable feeling for the user.

Figure 5:
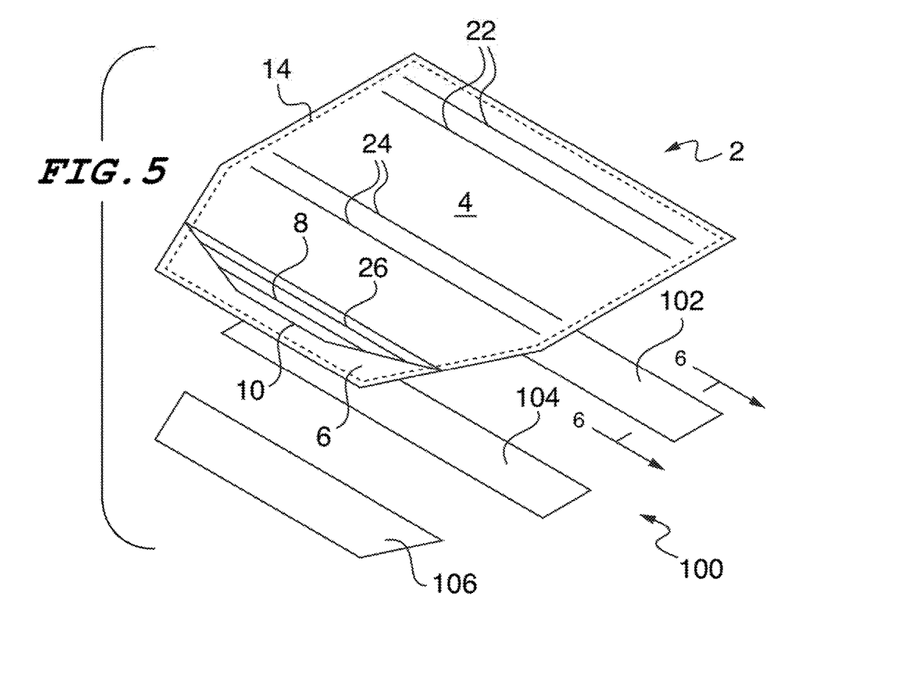
FIG. 5 is an isometric view of the adhesive strips being attached to the underside of the universal fit disposable seat pad, according to the present invention.

With respect to FIG. 5, there is illustrated a plurality of adhesive strips 100 being attached to the underside of base pad 4. In particular, adhesive strips 100, include adhesive strips 102, 104 and 106.

Figure 6:
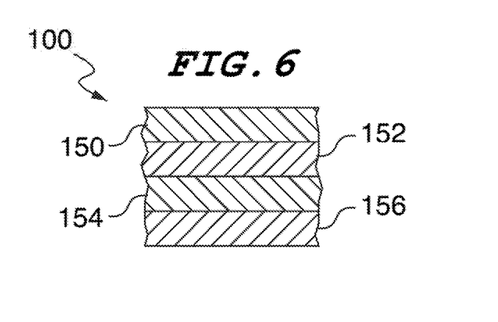
FIG. 6 is a side view of the adhesive strip layers, taken along lines 6-6 of FIG. 5, according to the present invention.

As shown in FIG. 6, preferably, adhesive strips 100 are constructed of a layer 150 of a synthetic acrylic adhesive, a carrier layer 152 of a polyethylene terephthalate (PET), an adhesive layer 154 of a synthetic acrylic adhesive (SAA), and a removable liner layer 156. Preferably, removable liner layer 156 can be constructed of a mono-axial oriented polypropylene (MOPP) however it is to be understood that other well-known backing layers can also be used. It is to be understood that the PET layer 152 acts a carrier layer for the adhesive layers 150 and 154 once the MOPP layer 156 has been removed from the adhesive strip 100. In this manner, once the MOPP layer 156 has been removed, a double-sided adhesive strip is created with layers 150, 152 and 154.

Furthermore, a still further unique aspect of the present invention is that the construction of the adhesive strips 100 is such that the adhesive layers 150 and 154 are more likely to remain adhered to the PET layer 152. This inventive aspect is very important since the adhesive layer 154 is the adhesive layer that is most likely to come into contact with the seat when the universal fit disposable seat pad 2 is placed on the seat. The construction of the adhesive strips 100 is such that if the universal fit disposable seat pad 2 needs to be removed from the seat, the adhesive in adhesive layer 154 will most likely stay attached to the PET layer 152 and not remain behind on the seat which is highly undesirable. For example, it is well known that adhesives stick to leather seats very easily. However, it is also known that once the adhesive has been removed from the leather seat, a portion of the adhesive typically remains behind on the leather seat, which is not desirable. The construction of the adhesive strips 100 of the present invention should substantially eliminate the possibility of the adhesive layer 154 remaining on the leather seat once the universal fit disposable seat pad 2 has been removed since the adhesive layer 154 wants to remain attached to the PET layer 152 and does not want to stay adhered to the leather seat. This feature is important since if universal fit disposable seat pad 2 is not soiled or otherwise comes into contact with any liquid, universal fit disposable seat pad 2 can be kept in place on the seat for several weeks.

With respect to the dimensions of the adhesive strips 100, as shown in FIG. 5, adhesive strip 102 is attached to a rear portion of the base pad 4. The adhesive strip 104 is attached to a mid-section of the base pad 4. The adhesive strip 106 is attached to a front portion of the base pad 4 and adjacent to the upper pad 8.

Another unique aspect of the present invention is the geometries of the adhesive strips 102, 104 and 106. As shown in FIG. 5, adhesive strip 102, preferably, is in the shape of a rectangle so that the adhesive strip 102 can be attached across a portion of the rear portion of the base pad 4. In this manner, adhesive strip 102 can be used to releasably secure base pad 4 to a section of the seat located towards the area where the seat and the seat back meet. Adhesive strip 104 preferably, is in the shape of a rectangle so that the adhesive strip 104 can attached across a portion of the mid-section portion of the base pad 4. In this manner, adhesive strip 104 can be used to releasably secure base pad 4 to a section of the seat located towards the middle of the seat. Finally, adhesive strip 106, preferably, is in the shape of a trapezoid so the adhesive strip 106 can attached across a portion of the front portion of the base pad 4 and adjacent to the upper pad 8. In this manner, adhesive strip 106 can be used to releasably secure base pad 4 to a section of the seat located towards the front area of base pad 4 where the seat and, possibly, where the seat buckle are located.

It is to be understood that with respect to adhesive strip 106, the location of adhesive strip 106 with respect to the front portion of base pad 4 and upper pad 8 is very important. The adhesive strip 106, preferably, should be located so that the trapezoid shape of adhesive strip 106 aligns with the front portion of base pad 4 and upper pad 8, as shown in FIG. 5. In this manner, the location of adhesive strip 106 does not create stress areas on base pad 4 and upper pad 8 once universal fit disposable seat pad 2 is attached to the seat. Also, it is to be understood that the shape of the front portion of base pad 4, the upper pad 8 and adhesive strip 106 substantially reduces the likelihood that universal fit disposable seat pad 2 will bunch up at the front end of universal fit disposable seat pad 2, especially if a seat belt buckle is utilized with universal fit disposable seat pad 2.

A still further unique aspect of the present invention is that the use of base pad 4 and adhesive strips 100 allows for base pad 4 to create a dam or blockage around the areas where the seat belts are located on a seat such as a car seat. It is known that in a typical 5-point harness car seat for infants and children, the seat belts are located on both sides of the infant/child, as the child sits in the car seat. The present invention creates a dam or blockage at those areas where the universal fit disposable seat pad 2 and the seat belts meet. In particular, once the universal fit disposable seat pad 2 has been installed on the seat such as a 5-point harness car seat, the areas of the universal fit disposable seat pad 2 located adjacent to the seat belts of the car seat will deflect inwardly towards the child/infant, thereby creating a blockage or dam at or near the seat belt to keep any liquids from contacting the seat belts and/or the orifices where the seat belts are connected to the car seat. This is because the adhesive strips 102 and 104 are located along the underside of base pad 4 in such a manner that the adhesive strips 102 and 104 do not come into contact with the areas around where the seat belts are located on the car seat.

As will be described in greater detail later, in order to attach the adhesive strips 100 to the underside of base pad 4, attention is directed to FIG. 5. As shown in FIG. 5, adhesive strips 102 and 104 are attached to base pad 4 by conventional stitches 22 and 24, respectively. Adhesive strip 106 is attached to base pad 4 and upper pad 8 by stitches 26. Another unique aspect of the present invention is the use of the stitches 22, 24 and 26. As will be described in greater detail later, during the construction of universal fit disposable seat pad 2, the adhesive strips 100 are attached to the underside of base pad 4, as previously discussed. After the adhesive strips 100 have been placed along the underside of base layer 4, as previously discussed, the adhesive strips 102, 104 and 106 are attached to the desired locations on the underside of base layer 4 so that the adhesive layer 150 of the adhesive strips 102, 104 and 106 comes into contact and becomes adhered to the underside of base layer 4. The adhesive layers 102 and 104 are then further secured to the underside of base layer 4 by stitches 22 and 24, respectively. The adhesive layer 106 is then further secured to the underside of base layer 4 and upper pad 8 by stitches 26.

With respect to the stitching design of stitches 22, 24, and 26, while these stitches are shown as being formed in a linear manner across the length of adhesives strips 102, 104 and 106, respectively, other layout designs of the stitches 22, 24 and 26 can also be utilized. An important point regarding the design of stitches 22, 24 and 26 is that the stitches 22, 24, and 26 must be able to provide a second level of securing the adhesives strips 100 to the underside of base pad 4 and not create any stress points while universal fit disposable seat pad 2 is attached to the seat and/or during the removal of universal fit disposable seat pad 2 from the seat. Furthermore, the stitches 22, 24 and 26 assist in keeping the adhesive strips 100 firmly attached to the universal fit disposable seat pad 2 while universal fit disposable seat pad 2 is attached to the seat and/or during the removal of universal fit disposable seat pad 2 from the seat.

Another unique aspect of the present invention is that the construction of universal fit disposable seat pad 2 is such that several of the universal fit disposable seat pads 2 can be conventionally folded and packaged in a compact and easily stored package. For example, 4-6 of the universal fit disposable seat pads 2 can be folded and placed in a package for commercial sale such that the package of universal fit disposable seat pads 2 can then be easily fit into the storage area located behind a front seat such as the driver's seat.

As shown in FIG. 7-10, there is illustrated universal fit disposable seat pad 202 that is constructed according to another embodiment of the present invention. Universal fit disposable seat pad 202 includes, in part, base pad 204, upper pad area 206, upper pad 208, upper pad area opening 210, base pad opening 212, peripheral pad stitching 214, upper pad stitching 216, upper pad stitching 218 and opening stitching 220.

Figure 7:
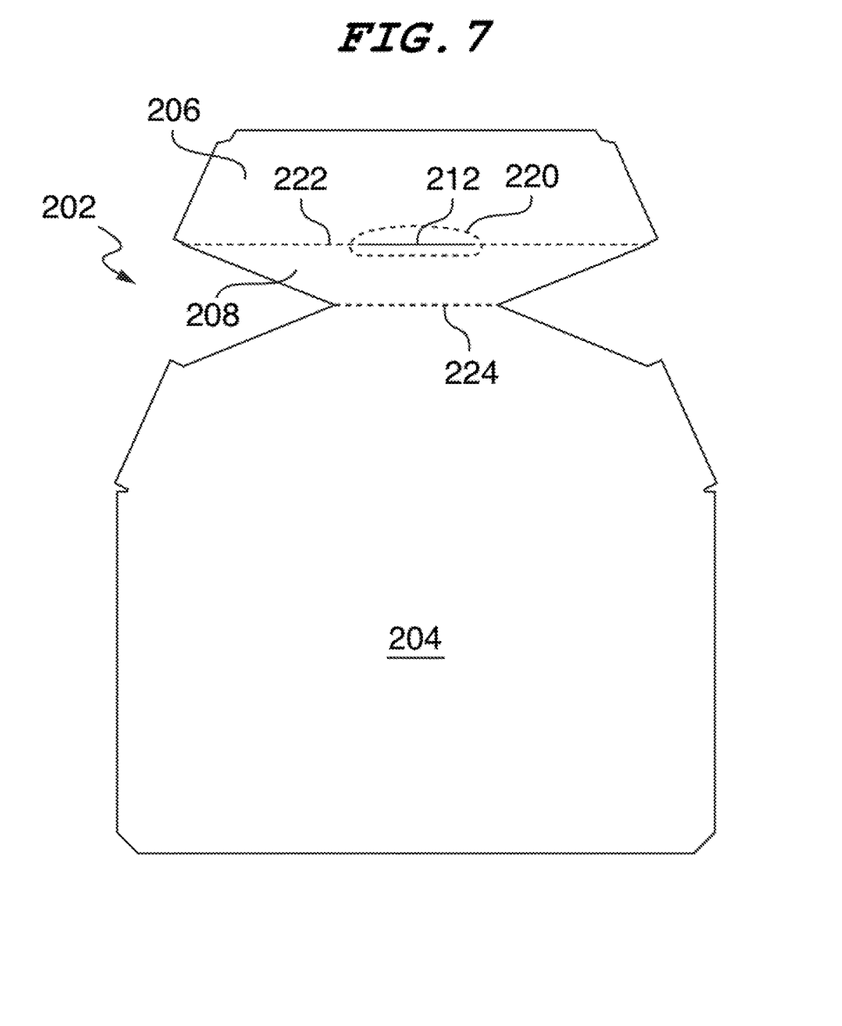
FIG. 7 is a top view of another embodiment of a base pad of a universal fit disposable seat pad, according to the present invention.

With respect to base pad 204 and upper pad area 206, as shown in FIG. 7, base pad 204 includes base pad opening 212. It is to be understood that base pad opening 212, preferably, is formed on base pad 4 by conventional cutting or forming techniques. A unique aspect of the present invention is that base pad opening 212 is formed in base pad 204 in order to allow a conventional seat belt buckle (not shown) to be placed through base pad opening 212, as will be discussed in greater detail later. It is to be further understood that a length and width of base pad 204 should be such that base pad 204 will properly fit over a conventional child's car seat or other types of seats while providing the proper protection against liquids and other bodily fluids including humans and/or animals.

Regarding the construction of base pad 204, it is to be understood that base pad 204 is constructed in a similar manner as base pad 4, as previously described. In particular, base pad 204 is constructed of several layers so that universal fit disposable seat pad 202 is able to absorb copious amounts of liquids. Also, base pad 204 includes opening stitching 220 which is formed on base pad 204 and acts in a similar manner as opening stitching 20 on base pad 4.

With respect to FIG. 7, there is illustrated upper pad area 206. It is to be understood that upper pad area 206 is constructed in substantially the same manner as base pad 4 and base pad 204. A still further unique aspect of the present invention is that upper pad area 206 is formed so that it can be secured to base pad 204 by upper pad stitches 216 and 218 (FIG. 8), as will be described in greater detail later.

Figure 8:
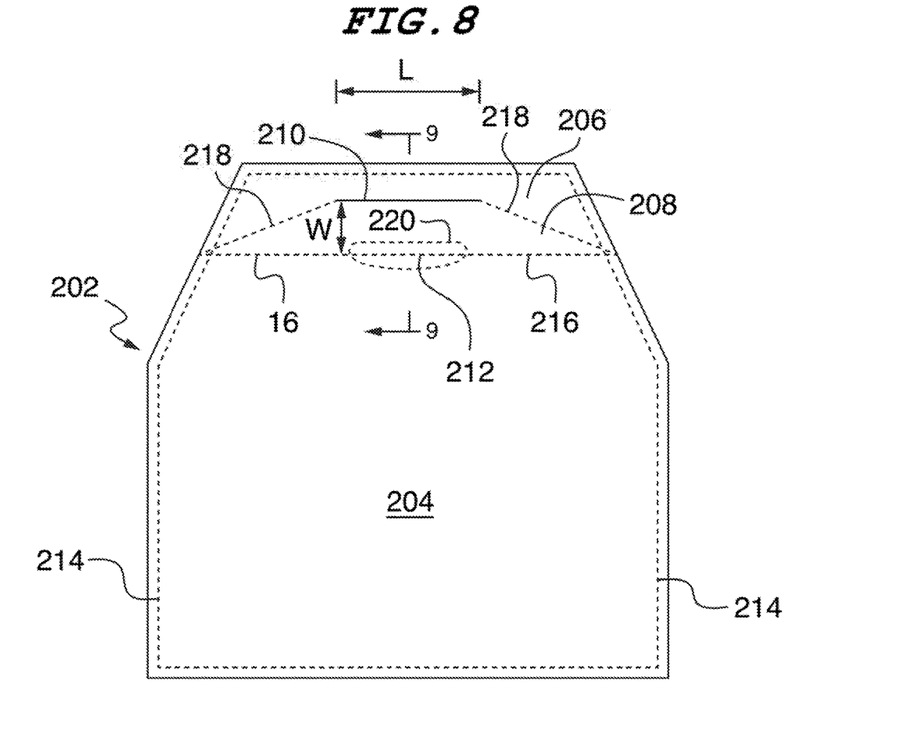
FIG. 8 is a top view of the second embodiment of the universal fit disposable seat pad, constructed according to the present invention.
Figure 9:
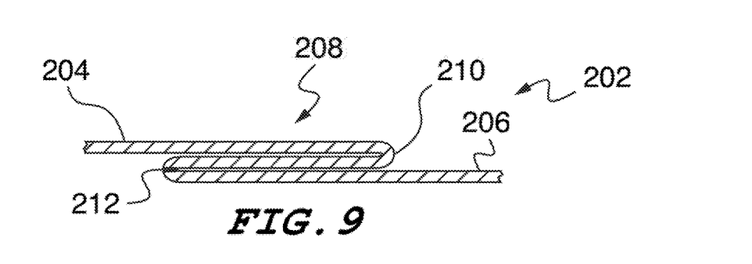
FIG. 9 is a side view of the second embodiment of the universal fit disposable seat pad layers, taken along lines 9-9 of FIG. 8, according to the present invention.

Regarding FIG. 8, there is illustrated universal fit disposable seat pad 202 with the upper pad area 206 being attached to base pad 204. As shown in FIGS. 7-9, upper pad area 206 is folded along fold lines 222 and 224 so that upper pad area 206 is folded under base pad 204 and upper pad 208 (FIG. 9). Base pad opening 212 is located under base pad 204 and upper pad 208 and upper pad area opening 210 is located on top of upper pad area 206. In this manner, upper pad area opening 210 and base pad opening 212 are aligned so that the seat belt buckle can be passed through base pad opening 212 and then through upper pad area opening 210. It is to be understood that once the base pad 204 and upper pad area 206 have been properly folded, as shown in FIGS. 8 and 9, upper pad area 206 and upper pad 208 are attached to base pad 204 by upper pad stitches 216 and 218. Preferably, upper pad stitches 216 and 218 are, preferably, an interlock-type of stitching but other well-known types of stitching can also be used. It is to be further understood that stitching 214 is located around a periphery of universal fit disposable seat pad 202. In this manner, stitching 214 is used to assist in keeping the various layers of base pad 204 attached together and provide an attractive edging for universal fit disposable seat pad 202.

Another unique aspect of the present invention is that universal fit disposable seat pad 202 includes upper pad area opening 210 and base pad opening 212. As discussed above, upper pad area opening 210 and base pad opening 212 are aligned on universal fit disposable seat pad 202 so as to allow a seat belt buckle (not shown) to be easily inserted through base pad opening 212 and then through upper pad area opening 210 so that the universal fit disposable seat pad 202 can be retained on the seat area of the seat and still allow the seat belt buckle to be operatively latched to the seat belt latch (not shown) so that the user of the seat can be securely retained in the seat.

A still further unique aspect of the present invention is that the use of upper pad area opening 210 and base pad opening 212 in conjunction with the seat belt buckle will create a blockage or dam around the area where the seat belt buckle interacts with the upper pad 208, the upper pad area opening 210 and base pad opening 212. In this manner, once the seat belt buckle has been inserted through upper pad area opening 210 and base pad opening 212, the locking of the seat belt buckle with the seat belt latch will cause the upper pad 208 to raise up and form a blockage or dam around the area located adjacent to the upper pad 208, upper pad area opening 210, the base pad opening 212 and the seat belt buckle. This blockage or dam should assist in keeping any liquids that come into contact with the universal fit disposable seat pad 202 from leaving the universal fit disposable seat pad 202 at the raised-up area around the upper pad area opening 210, the base pad opening 212 and the seat belt buckle. It is to be understood that if the length (L) of the upper pad 208 is too long, a blockage or dam may not form at the raised-up area around the upper pad 208, the upper pad area opening 210, the base pad opening 212 and the seat belt buckle. Conversely, if the length (L) is too short, the universal fit disposable seat pad 202 may inadvertently become removed from the seat when the seat belt buckle is attached to the seat belt latch, which is not desirable. Furthermore, if the width (W) of the upper pad 208 is too short, a blockage or dam may not form at the raised-up area around the upper pad 208, the upper pad area opening 210, the base pad opening 212 and the seat belt buckle. Conversely, if the width (W) is too long, the universal fit disposable seat pad 202 may inadvertently become bunched at the at the raised-up area around the upper pad 208, the upper pad area opening 210, the base pad opening 212 and the seat belt buckle which may cause an uncomfortable feeling for the user.

A yet even further unique aspect of the present invention is the use of opening stitching 220 around the base pad opening 212. In this manner, opening stitching 220 substantially prevents opening 212 from ripping or tearing once the seat belt buckle is inserted through base pad opening 212 by providing a reinforcement for base pad opening 212.

Figure 10:
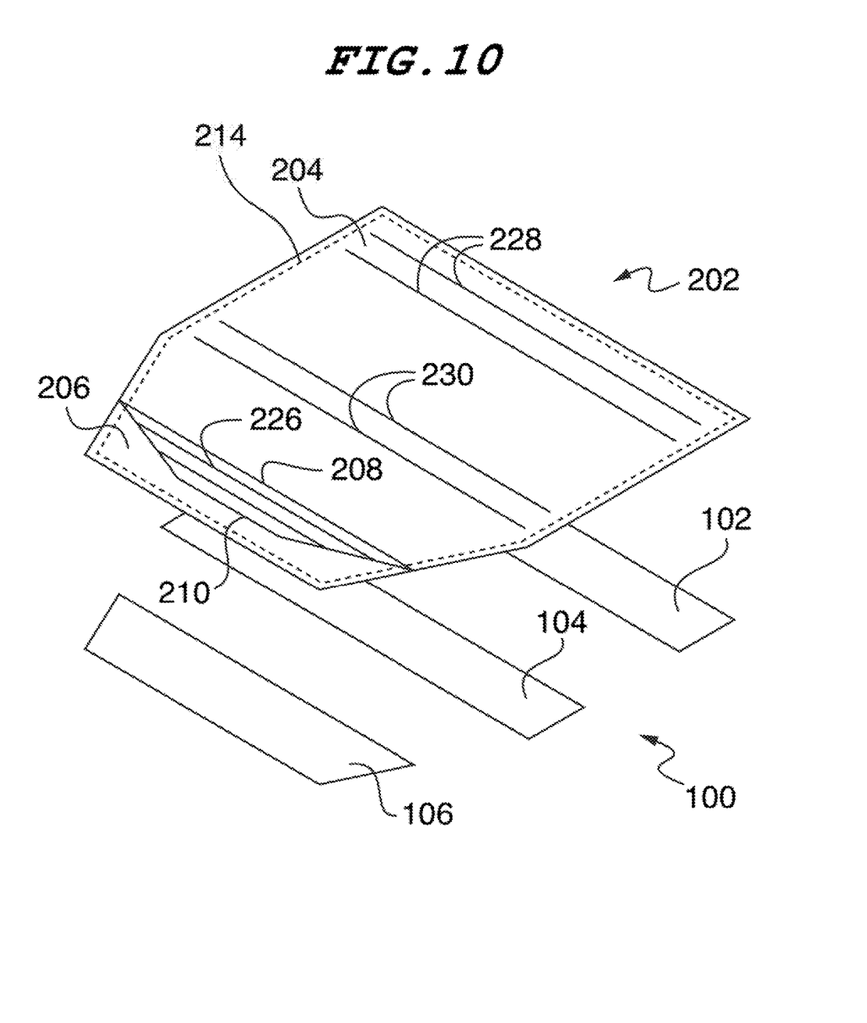
FIG. 10 is an isometric view of the adhesive strips being attached to the second embodiment of the universal fit disposable seat pad, according to the present invention.

With respect to FIG. 10, there is illustrated a plurality of adhesive strips 100 being attached to the underside of base pad 204. In particular, adhesive strips 100, include adhesive strips 102, 104 and 106. It is to be understood that adhesive strips 100 should be the same adhesive strips 100 used in conjunction with base pad 4 and upper pad 8 (FIG. 5).

With respect to the dimensions of the adhesive strips 100, as shown in FIG. 10, adhesive strip 102 is attached to a rear portion of the base pad 204. The adhesive strip 104 is attached to a mid-section of the base pad 204. The adhesive strip 106 is attached to a front portion of the base pad 204 and adjacent to the upper pad 208.

Another unique aspect of the present invention is the geometries of the adhesive strips 102, 104 and 106. As shown in FIG. 10, adhesive strip 102, preferably, is in the shape of a rectangle so that the adhesive strip 102 can be attached across a portion of the rear portion of the base pad 204. In this manner, adhesive strip 102 can be used to releasably secure base pad 204 to a section of the seat located towards the area where the seat and the seat back meet. Adhesive strip 104 preferably, is in the shape of a rectangle so that the adhesive strip 104 can attached across a portion of the mid-section portion of the base pad 204. In this manner, adhesive strip 104 can be used to releasably secure base pad 204 to a section of the seat located towards the middle of the seat. Finally, adhesive strip 106, preferably, is in the shape of a trapezoid so the adhesive strip 106 can attached across a portion of the front portion of the base pad 204 adjacent to upper pad 208. In this manner, adhesive strip 106 can be used to releasably secure base pad 204 to a section of the seat located towards the front area where the seat and, possibly, where the seat buckle are located.

It is to be understood that with respect to adhesive strip 106, the location of adhesive strip 106 with respect to the front portion of base pad 204 and upper pad 208 is very important. The adhesive strip 106, preferably, should be located so that the trapezoid shape of adhesive strip 106 aligns with the front portion of base pad 204 and upper pad 208, as shown in FIG. 10. In this manner, the location of adhesive strip 106 does not create stress areas on base pad 204 and upper pad 208 once universal fit disposable seat pad 202 is attached to the seat. Also, it is to be understood that the shape of the front portion of base pad 204, the upper pad 208 and adhesive strip 106 substantially reduces the likelihood that universal fit disposable seat pad 202 will bunch up at the front end of universal fit disposable seat pad 202, especially if a seat belt buckle is utilized with universal fit disposable seat pad 202.

A still further unique aspect of the present invention is that the use of base pad 204 and adhesive strips 100 allows for base pad 204 to create a dam or blockage around the areas where the seat belts are located on a seat such as a car seat. It is known that in a typical 5-point harness car seat for infants and children, the seat belts are located on both sides of the infant/child, as the child sits in the car seat. The present invention creates a dam or blockage at those areas where the universal fit disposable seat pad 202 and the seat belts meet. In particular, once the universal fit disposable seat pad 202 has been installed on the seat such as a 5-point harness car seat, the areas of the universal fit disposable seat pad 202 located adjacent to the seat belts of the car seat will deflect inwardly towards the child/infant, thereby creating a blockage or dam at or near the seat belt to keep any liquids from contacting the seat belts and/or the seat belt orifices where the seat belts are connected to the seat. This is because the adhesive strips 102 and 104 are located along the underside of base pad 204 in such a manner that the adhesive strips 102 and 104 do not come into contact with the areas around where the seat belts are located on the car seat.

As will be described in greater detail later, in order to attach the adhesive strips 100 to the underside of base pad 204 and upper pad 208, attention is directed to FIG. 10. As shown in FIG. 10, adhesive strips 102 and 104 are attached to base pad 204 by conventional stitches 228 and 230, respectively. Adhesive strip 106 is attached to base pad 204 and upper pad 208 by stitches 226. Another unique aspect of the present invention is the use of the stitches 226, 228 and 230. As will be described in greater detail later, during the construction of universal fit disposable seat pad 202, the adhesive strips 100 are attached to the underside of base pad 204, as previously discussed. In this manner, the adhesive layer 150 of adhesive layers 100 comes into contact and becomes adhered to the underside of base layer 204. After the adhesive strips 100 have been placed along the underside of base layer 204, as previously discussed, the adhesive strips 102, 104 and 106 are attached to the desired locations on the underside of base layer 204 so that the adhesive layer 150 of the adhesive strips 102, 104 and 106 comes into contact and becomes adhered to the underside of base layer 204. The adhesive layers 102 and 104 are then further secured to the underside of base layer 204 by stitches 228 and 230, respectively. The adhesive layer 106 is then further secured to the underside of base layer 204 and upper pad 208 by stitches 226.

With respect to the stitching design of stitches 228, 230, and 226, while these stitches are shown as being formed in a linear manner across the length of adhesives strips 102, 104 and 106, respectively, other layout designs of the stitches 228, 230 and 226 can also be utilized. An important point regarding the design of stitches 228, 230, and 226 is that the stitches 228, 230 and 226 must be able to provide a second level of securing the adhesives strips 100 to base pad 204 and upper pad 208 and not create any stress points while universal fit disposable seat pad 202 is attached to the seat and/or during the removal of universal fit disposable seat pad 202 from the seat. Furthermore, the stitches 228, 230, and 226 assist in keeping the adhesive strips 100 firmly attached to the universal fit disposable seat pad 202 while universal fit disposable seat pad 202 is attached to the seat and/or during the removal of universal fit disposable seat pad 202 from the seat.

With reference now to FIG. 1-10, the operation and use of universal fit disposable seat pad 2 and/or 202 will now be discussed. After universal fit disposable seat pad 2 or 202 has been formed (i.e., the upper pad 8 is attached to base pad 4 in universal fit disposable seat pad 2 by 16 and 18 and stitches 14 are added to base pad 4 or the base pad 204 and upper pad area 206 are folded to create base pad 204 and upper pad 208 and upper pad area 206 is attached to base pad 204 by stitches 216 and 218 and stitches 214 are added to base pad 204), the adhesive strips 100 are attached to the underside of base pads 4 or 204.

After the adhesives strips 100 have been attached to base pads 4 and 204, the adhesive strips 100 are further attached to base pads 4, 204 and upper pads 8 and 208 with stitches 22, 24, 26 and 228, 230, and 226, respectively.

Once the stitches 22, 24, 26 or 228, 230 226 have been applied to base pads 4 and 204 and upper pads 8 and 208, respectively, the liner layer 156 is removed from adhesive strips 100. After the liner layers 156 have been removed, the universal fit disposable seat pad 2 and 202 are placed on the seat and secured to the seat by pressing the universal fit disposable seat pad 2 or 202 down onto the seat, especially in the areas where the adhesive strips 100 are located on the underside of universal fit disposable seat pad 2 or 202. The stitching patterns of stitches 22/24/26 or 228/230/226 aid in assisting the user in determining where the adhesive strips 100 are located on the underside of universal fit disposable seat pad 2 or 202.

If the universal fit disposable seat pad 2 and 202 becomes soiled or otherwise needs to be removed and changed, the end user simply has to pull up on the corners of universal fit disposable seat pad 2 and 202 in order to remove the universal fit disposable seat pad 2 or 202 from the seat. The end user can then discard the used universal fit disposable seat pad 2 or 202 in a conventional manner.

The preceding merely illustrates the principles of the invention. It will thus be appreciated that those skilled in the art will be able to devise various arrangements which, although not explicitly described or shown herein, embody the principles of the invention and are included within its spirit and scope. Furthermore, all examples and conditional language recited herein are principally intended expressly to be only for pedagogical purposes and to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention, as well as specific examples thereof, are intended to encompass both structural and functional equivalents thereof. Additionally, it is intended that such equivalents include both currently known equivalents and equivalents developed in the future, i.e., any elements developed that perform the same function, regardless of structure.

This description of the exemplary embodiments is intended to be read in connection with the figures of the accompanying drawing, which are to be considered part of the entire written description. In the description, relative terms such as "lower," "upper," "horizontal," "vertical," "above," "below," "up," "down," "top" and "bottom" as well as derivatives thereof (e.g., "horizontally," "downwardly," "upwardly," etc.) should be construed to refer to the orientation as then described or as shown in the drawing under discussion. These relative terms are for convenience of description and do not require that the apparatus be constructed or operated in a particular orientation. Terms concerning attachments, coupling and the like, such as "connected" and "interconnected," refer to a relationship wherein structures are secured or attached to one another either directly or indirectly through intervening structures, as well as both movable or rigid attachments or relationships, unless expressly described otherwise.

All patents, publications, scientific articles, web sites, and other documents and materials referenced or mentioned herein are indicative of the levels of skill of those skilled in the art to which the invention pertains, and each such referenced document and material is hereby incorporated by reference to the same extent as if it had been incorporated by reference in its entirety individually or set forth herein in its entirety.

The applicant reserves the right to physically incorporate into this specification any and all materials and information from any such patents, publications, scientific articles, web sites, electronically available information, and other referenced materials or documents to the extent such incorporated materials and information are not inconsistent with the description herein.

The written description portion of this patent includes all claims. Furthermore, all claims, including all original claims as well as all claims from any and all priority documents, are hereby incorporated by reference in their entirety into the written description portion of the specification, and Applicant(s) reserve the right to physically incorporate into the written description or any other portion of the application, any and all such claims. Thus, for example, under no circumstances may the patent be interpreted as allegedly not providing a written description for a claim on the assertion that the precise wording of the claim is not set forth in haec verba in written description portion of the patent.

The claims will be interpreted according to law. However, and notwithstanding the alleged or perceived ease or difficulty of interpreting any claim or portion thereof, under no circumstances may any adjustment or amendment of a claim or any portion thereof during prosecution of the application or applications leading to this patent be interpreted as having forfeited any right to any and all equivalents thereof that do not form a part of the prior art.

All of the features disclosed in this specification may be combined in any combination. Thus, unless expressly stated otherwise, each feature disclosed is only an example of a generic series of equivalent or similar features.

It is to be understood that while the invention has been described in conjunction with the detailed description thereof, the foregoing description is intended to illustrate and not limit the scope of the invention, which is defined by the scope of the appended claims. Thus, from the foregoing, it will be appreciated that, although specific embodiments of the invention have been described herein for the purpose of illustration, various modifications may be made without deviating from the spirit and scope of the invention. Other aspects, advantages, and modifications are within the scope of the following claims and the present invention is not limited except as by the appended claims.

The specific methods and compositions described herein are representative of preferred embodiments and are exemplary and not intended as limitations on the scope of the invention. Other objects, aspects, and embodiments will occur to those skilled in the art upon consideration of this specification, and are encompassed within the spirit of the invention as defined by the scope of the claims. It will be readily apparent to one skilled in the art that varying substitutions and modifications may be made to the invention disclosed herein without departing from the scope and spirit of the invention. The invention illustratively described herein suitably may be practiced in the absence of any element or elements, or limitation or limitations, which is not specifically disclosed herein as essential. Thus, for example, in each instance herein, in embodiments or examples of the present invention, the terms "comprising", "including", "containing", etc. are to be read expansively and without limitation. The methods and processes illustratively described herein suitably may be practiced in differing orders of steps, and that they are not necessarily restricted to the orders of steps indicated herein or in the claims.

The terms and expressions that have been employed are used as terms of description and not of limitation, and there is no intent in the use of such terms and expressions to exclude any equivalent of the features shown and described or portions thereof, but it is recognized that various modifications are possible within the scope of the invention as claimed. Thus, it will be understood that although the present invention has been specifically disclosed by various embodiments and/or preferred embodiments and optional features, any and all modifications and variations of the concepts herein disclosed that may be resorted to by those skilled in the art are considered to be within the scope of this invention as defined by the appended claims.

The invention has been described broadly and generically herein. Each of the narrower species and sub-generic groupings falling within the generic disclosure also form part of the invention. This includes the generic description of the invention with a proviso or negative limitation removing any subject matter from the genus, regardless of whether or not the excised material is specifically recited herein.

It is also to be understood that as used herein and in the appended claims, the singular forms "a," "an," and "the" include plural reference unless the context clearly dictates otherwise, the term "X and/or Y" means "X" or "Y" or both "X" and "Y", and the letter "s" following a noun designates both the plural and singular forms of that noun. In addition, where features or aspects of the invention are described in terms of Markush groups, it is intended and those skilled in the art will recognize, that the invention embraces and is also thereby described in terms of any individual member or subgroup of members of the Markush group.

Other embodiments are within the following claims. Therefore, the patent may not be interpreted to be limited to the specific examples or embodiments or methods specifically and/or expressly disclosed herein. Under no circumstances may the patent be interpreted to be limited by any statement made by any Examiner or any other official or employee of the Patent and Trademark Office unless such statement is specifically and without qualification or reservation expressly adopted in a responsive writing by Applicants.

Although the invention has been described in terms of exemplary embodiments, it is not limited thereto. Rather, the appended claims should be construed broadly, to include other variants and embodiments of the invention, which may be made by those skilled in the art without departing from the scope and range of equivalents of the invention.

Other modifications and implementations will occur to those skilled in the art without departing from the spirit and the scope of the invention as claimed. Accordingly, the description hereinabove is not intended to limit the invention, except as indicated in the appended claims.

Therefore, provided herein are a new and improved universal fit disposable seat pad. The preferred universal fit disposable seat pad, according to various embodiments of the present invention, offers the following advantages: ease of use; lightness in weight; durability; the ability to use the disposable seat pad on a variety of different types and sizes of seats; the ability of the disposable seat pad to provide seat protection against liquids and other bodily fluids including humans and/or animals; the use of strategically located adhesive strips that releasably secure the pad in place in order to provide a universal fit for the pad on the seat; the use of a super absorbent polymer that allows the disposable pad to absorb copious amounts of liquids; the disposable pad is shaped in such a manner so that the pad forms a "cup" when the pad is placed in a conventional children's car seat while also conforming to any other seat that an adult or child may use; the disposable pad is designed so that it does not interfere with the car seat straps while still preventing liquids from flowing into the car seat strap orifices; the disposable pad fits most current children's car seats, boosters etc. giving users confidence that it will fit the seat they own; the geometry and materials of the disposable pad allow for many seat pads to be stored together in a small place, such as the storage pocket on the back of the driver's seat; and the disposable pad is constructed from materials that are acceptable to most municipal waste sites. In fact, in many of the preferred embodiments, these advantages of ease of use, lightness in weight, durability, the ability to use the disposable seat pad on a variety of different types and sizes of seats, the ability of the disposable seat pad to provide seat protection against liquids and other bodily fluids including humans and/or animals, the use of strategically located adhesive strips that releasably secure the pad in place in order to provide a universal fit for the pad on the seat, the use of a super absorbent polymer that allows the disposable pad to absorb copious amounts of liquids, the disposable pad is shaped in such a manner so that the pad forms a "cup" when the pad is placed in a conventional children's car seat while also conforming to any other seat that an adult or child may use, the disposable pad is designed so that it does not interfere with the car seat straps while still preventing liquids from flowing into the car seat strap orifices, the disposable pad fits most current children's car seats, boosters etc. giving users confidence that it will fit the seat they own, the geometry and materials of the disposable pad allow for many seat pads to be stored together in a small place, such as the storage pocket on the back of the driver's seat, and the disposable pad is constructed from materials that are acceptable to most municipal waste sites are optimized to an extent that is considerably higher than heretofore achieved in prior, known disposable seat pads.

We claim:

1. A seat protection pad to protect a seat against spilled liquids and other bodily fluids including human and animal fluids, comprising:
    a multi-layered base pad, wherein the multi-layered base pad includes a first side and a second side and a front portion, a mid-section portion and a rear portion, wherein the multi-layered base pad includes a base pad opening located between the mid-section portion and the front portion;
    a multi-layered upper pad, wherein the multi-layered upper pad includes a first side and a second side and a front end and a rear end, wherein the multi-layered upper pad is located adjacent to the front portion of the multi-layered base pad in order to allow the multi-layered upper pad to be located over only the front portion of the multi-layered base pad, and wherein the multi-layered upper pad is stitched to the first side of the multi-layered base pad at a location adjacent to the front portion of the multi-layered base pad such that the second side of the multi-layered upper pad is located adjacent to the first side of the multi-layered base pad;
    an upper pad opening located between the front end of the multi-layered upper pad and the front portion of the multi-layered base pad such that the upper pad opening is aligned with the base pad opening to allow a seat belt buckle to be inserted through the base pad opening and the upper pad opening;
    a plurality of adhesive strips located on the second side of the multi-layered base pad, wherein a first one of the plurality of adhesive strips is attached adjacent to the rear portion of the multi-layered base pad, a second one of the plurality of adhesive strips is attached adjacent to the mid-section portion of the multi-layered base pad and a third one of the plurality of adhesive strips is attached adjacent to the front portion of the multi-layered base pad; and
    a plurality of stitches located on the multi-layered base pad and the multi-layered upper pad for securing the multi-layered base pad and the multi-layered upper pad together, wherein the plurality of stitches are used to secure the plurality of adhesive strips to the second side of the multi-layered base pad.

2. A seat protection pad to protect a seat against spilled liquids and other bodily fluids including human and animal fluids, comprising:
    a multi-layered base pad, wherein the multi-layered base pad includes a first side and a second side and a front portion, a mid-section portion and a rear portion, wherein the multi-layered base pad includes a base pad opening located between the mid-section portion and the front portion;
    a multi-layered upper pad, wherein the multi-layered upper pad includes a first side and a second side and a front end and a rear end, wherein the multi-layered upper pad is located adjacent to the front portion of the multi-layered base pad in order to allow the multi-layered upper pad to be located over only the front portion of the multi-layered base pad, and wherein the multi-layered upper pad is stitched to the first side of the multi-layered base pad at a location adjacent to the front portion of the multi-layered base pad such that the second side of the multi-layered upper pad is located adjacent to the first side of the multi-layered base pad;
    an upper pad opening located between the front end of the multi-layered upper pad and the front portion of the multi-layered base pad such that the upper pad opening is aligned with the base pad opening to allow a seat belt buckle to be inserted through the base pad opening and the upper pad opening, wherein when the seat belt buckle is operatively connected to a seat belt latch, the connection of the seat belt buckle to the seat belt latch will cause the multi-layered upper pad to raise up and form a blockage around an area located adjacent to the multi-layered upper pad, the upper pad opening, the base pad opening and the seat belt buckle in order to assist in keeping any liquids that come into contact with the seat protection pad from leaving the seat protection pad at the blockage;
    a plurality of adhesive strips located on the second side of the multi-layered base pad, wherein a first one of the plurality of adhesive strips is attached adjacent to the rear portion of the multi-layered base pad, a second one of the plurality of adhesive strips is attached adjacent to the mid-section portion of the multi-layered base pad and a third one of the plurality of adhesive strips is attached adjacent to the front portion of the multi-layered base pad; and
    a plurality of stitches located on the multi-layered base pad and the multi-layered upper pad for securing the multi-layered base pad and the multi-layered upper pad together, wherein the plurality of stitches are used to secure the plurality of adhesive strips to the second side of the multi-layered base pad.

3. The seat protection pad, according to claim 2, wherein the base pad and the upper pad are further comprised of:
    a non-woven layer;
    a first tissue cellulose layer located adjacent to the non-woven layer;
    a super absorbent polymer layer located adjacent to the first tissue cellulose layer;
    a second tissue cellulose layer located adjacent to the super absorbent polymer layer, and
    a liquid barrier layer located adjacent to the second cellulose layer.

4. The seat protection pad, according to claim 3, wherein the non-woven layer is further comprised of:
    polypropylene.

5. The seat protection pad, according to claim 3, wherein the super absorbent polymer layer is further comprised of:
a fiber fluff cellulose pulp.

6. The seat protection pad, according to claim 3, wherein the liquid barrier layer is further comprised of:
polyethylene.

7. The seat protection pad, according to claim 2, wherein the plurality of adhesive strips is further comprised of:
a first adhesive layer;
a carrier layer located adjacent to the first adhesive layer;
a second adhesive layer located adjacent to the carrier layer; and
a removable liner layer located adjacent to the second adhesive layer.

8. The seat protection pad, according to claim 7, wherein the first adhesive layer is further comprised of:
a synthetic acrylic adhesive (SAA).

9. The seat protection pad, according to claim 7, wherein the carrier layer is further comprised of:
polyethylene terephthalate (PET).

10. The seat protection pad, according to claim 7, wherein the second adhesive layer is further comprised of:
a synthetic acrylic adhesive (SAA).

11. The seat protection pad, according to claim 7, wherein the removable liner layer is further comprised of:
a mono-axial oriented polypropylene (MOPP).

12. A multi-layered, disposable, fluid collection pad, comprising:
a multi-layered base pad, wherein the multi-layered base pad includes a first side and a second side and a front portion, a mid-section portion and a rear portion, wherein the multi-layered base pad includes a base pad opening located between the mid-section portion and the front portion;
a multi-layered upper pad, wherein the multi-layered upper pad includes a first side and a second side and a front end and a rear end, wherein the multi-layered upper pad is located adjacent to the front portion of the multi-layered base pad in order to allow the multi-layered upper pad to be located over the front portion of the multi-layered base pad, and wherein the multi-layered upper pad is stitched to the first side of the multi-layered base pad at a location adjacent to the front portion of the multi-layered base pad such that the second side of the multi-layered upper pad is located adjacent to the first side of the multi-layered base pad;
an upper pad opening located between the front end of the multi-layered upper pad and the front portion of the multi-layered base pad such that the upper pad opening is aligned with the base pad opening to allow a seat belt buckle to be inserted through the base pad opening and the upper pad opening, wherein when the seat belt buckle is operatively connected to a seat belt latch, the connection of the seat belt buckle to the seat belt latch causes the multi-layered upper pad to raise up and form a blockage around an area located adjacent to the multi-layered upper pad, the upper pad opening, the base pad opening and the seat belt buckle in order to assist in keeping any liquids that come into contact with the seat protection pad from leaving the seat protection pad at the blockage;
a plurality of adhesive strips comprising a first adhesive layer; a carrier layer located adjacent to the first adhesive layer; a second adhesive layer located adjacent to the carrier layer; and a removable liner layer located adjacent to the second adhesive located on the second side of the multi-layered base pad, wherein a first one of the plurality of adhesive strips is attached adjacent to the rear portion of the multi-layered base pad, a second one of the plurality of adhesive strips is attached adjacent to the mid-section portion of the multi-layered base pad and a third one of the plurality of adhesive strips is attached adjacent to the front portion of the multi-layered base pad; and
a plurality of stitches located on the multi-layered base pad and the multi-layered upper pad for securing the multi-layered base pad and the multi-layered upper pad together, wherein the plurality of stitches are used to secure the plurality of adhesive strips to the second side of the multi-layered base pad.

13. The multi-layered, disposable seat pad, according to claim 12, wherein the base pad and the upper pad are further comprised of:
a non-woven layer;
a first tissue cellulose layer located adjacent to the non-woven layer;
a super absorbent polymer layer located adjacent to the first tissue cellulose layer;
a second tissue cellulose layer located adjacent to the super absorbent polymer layer; and
a liquid barrier layer located adjacent to the second cellulose layer.

14. The multi-layered, disposable seat pad, according to claim 13, wherein the non-woven layer is further comprised of:
polypropylene.

15. The multi-layered, disposable seat pad, according to claim 13, wherein the super absorbent polymer layer is further comprised of:
a fiber fluff cellulose pulp.

16. The multi-layered, disposable seat pad, according to claim 13, wherein the liquid barrier layer is further comprised of:
polyethylene.

17. The multi-layered, disposable seat pad, according to claim 11, wherein the first adhesive layer is further comprised of:
a synthetic acrylic adhesive (SAA).

18. The multi-layered, disposable seat pad, according to claim 11, wherein the carrier layer is further comprised of:
polyethylene terephthalate (PET).

19. The multi-layered, disposable seat pad, according to claim 11, wherein the second adhesive layer is further comprised of:
a synthetic acrylic adhesive (SAA).

\* \* \* \* \*